(12) United States Patent
Brown et al.

(10) Patent No.: US 11,402,385 B2
(45) Date of Patent: Aug. 2, 2022

(54) MASS SPECTROMETRY FOR DETERMINING IF A MUTATED VARIANT OF A TARGET PROTEIN IS PRESENT IN A SAMPLE

(71) Applicant: Micromass UK Limited, Wilmslow (GB)

(72) Inventors: Jeffery Mark Brown, Hyde (GB); Michael Raymond Morris, Glossop (GB); Jonathan Williams, West Glamorgan (GB); Brian Green, Sale (GB)

(73) Assignee: MICROMASS UK LIMITED, Wilmslow (GB)

( * ) Notice: Subject to any disclaimer, the term of this patent is extended or adjusted under 35 U.S.C. 154(b) by 499 days.

(21) Appl. No.: 15/516,083

(22) PCT Filed: Oct. 1, 2015

(86) PCT No.: PCT/GB2015/052881
§ 371 (c)(1),
(2) Date: Mar. 31, 2017

(87) PCT Pub. No.: WO2016/051191
PCT Pub. Date: Apr. 7, 2016

(65) Prior Publication Data
US 2017/0292960 A1    Oct. 12, 2017

(30) Foreign Application Priority Data

Oct. 1, 2014 (GB) .................................. 1417387

(51) Int. Cl.
*G01N 33/68* (2006.01)
*G01N 33/72* (2006.01)
(Continued)

(52) U.S. Cl.
CPC ......... *G01N 33/6848* (2013.01); *G01N 33/68* (2013.01); *G01N 33/721* (2013.01);
(Continued)

(58) Field of Classification Search
CPC ........... G01N 33/6648; G01N 33/6818; G01N 33/6848; G01N 33/721; G01N 33/723;
(Continued)

(56) References Cited

U.S. PATENT DOCUMENTS 6,017,693 A    1/2000 Yates, III et al.
7,838,303 B2    11/2010 Perkins et al.
(Continued)

FOREIGN PATENT DOCUMENTS

WO    01/84137    11/2001
WO    2004/090552    10/2004
(Continued)

OTHER PUBLICATIONS

Théberge, R. et al. "Top-down analysis of small plasma proteins using an LTQ-Orbitrap. Potential for mass spectrometry-based clinical assays for transthyretin and hemoglobin," International Journal of Mass Spectrometry 300 (2011) 130-142 (Year: 2011).*
(Continued)

*Primary Examiner* — Jennifer Wecker
*Assistant Examiner* — Michelle Adams
(74) *Attorney, Agent, or Firm* — Deborah M. Vernon; Mark R. Deluca

(57) ABSTRACT

A method of mass spectrometry determines if a mutated variant of a target protein is present in a sample. The method includes subjecting the sample to fragmentation so as to cause the target protein to fragment to form second generation fragment ions, and then mass analysing these fragment ions to obtain spectral data. The method determines if a mutated variant is present in the sample by determining that
(Continued)

an ion in the spectral data has a mass to charge ratio that differs from the mass to charge ratio of an ion that would be observed if the target protein was a normal unmutated version of the target protein, and by an amount that corresponds to a mass difference that would be caused by the target protein being a mutated variant of the target protein.

15 Claims, 4 Drawing Sheets

(51) Int. Cl.
*H01J 49/00* (2006.01)
*G01N 33/48* (2006.01)

(52) U.S. Cl.
CPC ......... *G01N 33/48* (2013.01); *G01N 33/6818* (2013.01); *G01N 33/6842* (2013.01); *H01J 49/0054* (2013.01); *H01J 49/0072* (2013.01)

(58) Field of Classification Search
CPC . H01J 49/0045; H01J 49/0054; H01J 49/0072
See application file for complete search history.

(56) References Cited

U.S. PATENT DOCUMENTS

| | | | |
|---|---|---|---|
| 8,153,961 | B2 | 4/2012 | Zabrouskov |
| 8,278,115 | B2 | 10/2012 | Coon et al. |
| 9,046,527 | B2 | 6/2015 | Galisson et al. |
| 9,347,084 | B2 | 5/2016 | Turner et al. |
| 2006/0255261 | A1* | 11/2006 | Whitehouse ........ H01J 49/0431 250/288 |
| 2008/0280345 | A1* | 11/2008 | Turner ............... G01N 33/6848 435/219 |
| 2011/0303839 | A1* | 12/2011 | Robb .................. H01J 49/0054 250/282 |
| 2013/0210050 | A1 | 8/2013 | Kelleher et al. |
| 2015/0111238 | A1 | 4/2015 | Tang et al. |
| 2017/0108508 | A1* | 4/2017 | Geromanos ........... H01J 49/421 |
| 2017/0162372 | A1* | 6/2017 | Stephenson, Jr ........ C12Q 1/04 |

FOREIGN PATENT DOCUMENTS

| | | | | |
|---|---|---|---|---|
| WO | WO-2013112677 | A2 * | 8/2013 | |
| WO | WO-2013171493 | A2 * | 11/2013 | .......... H01J 49/0077 |
| WO | 2015150785 | A1 | 10/2015 | |

OTHER PUBLICATIONS

Robb, D.B. et al. "Tandem Mass Spectrometry Using the Atmospheric Pressure Electron Capture Dissociation Ion Source," Anal. Chem. 2014, 86, 4439-4446; Apr. 2, 2014. (Year: 2014).*
Han, H. et al. "Ion Trap Collisional Activation of c and z• Ions Formed via Gas-Phase Ion/Ion Electron-Transfer Dissociation," J. Proteome Res. 2007, 6, 8, 3062-3069. Including graphical abstract. (Year: 2007).*
Graça, et al., "Electron Transfer Dissociation Mass Spectronomy of Hemoglobin on Clinical Samples", Journal of American Society for Mass Spectronomy, vol. 23, No. 10, pp. 1750-1756, 2012.

* cited by examiner

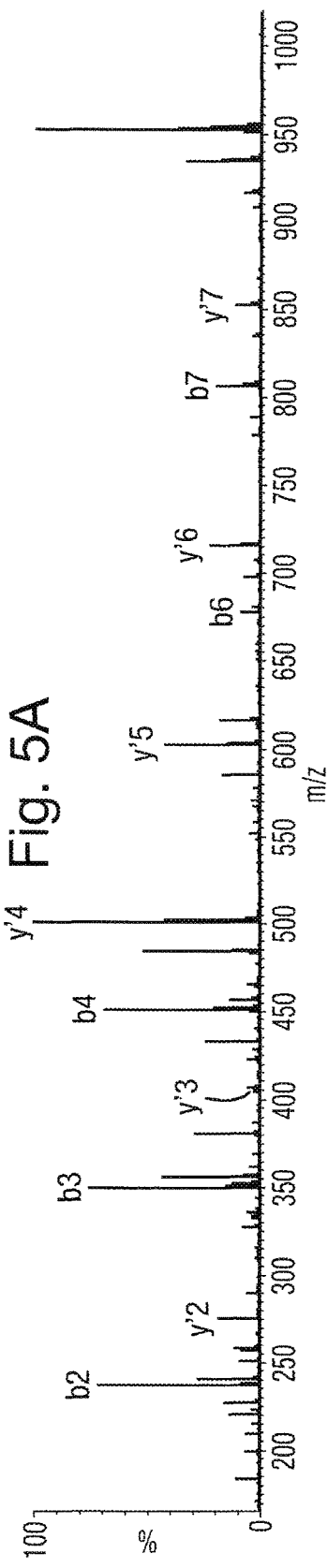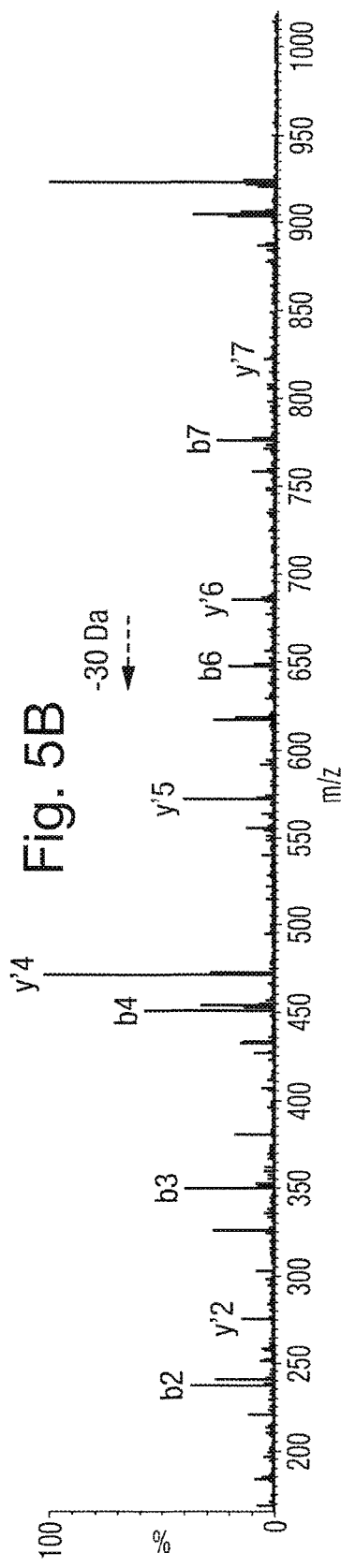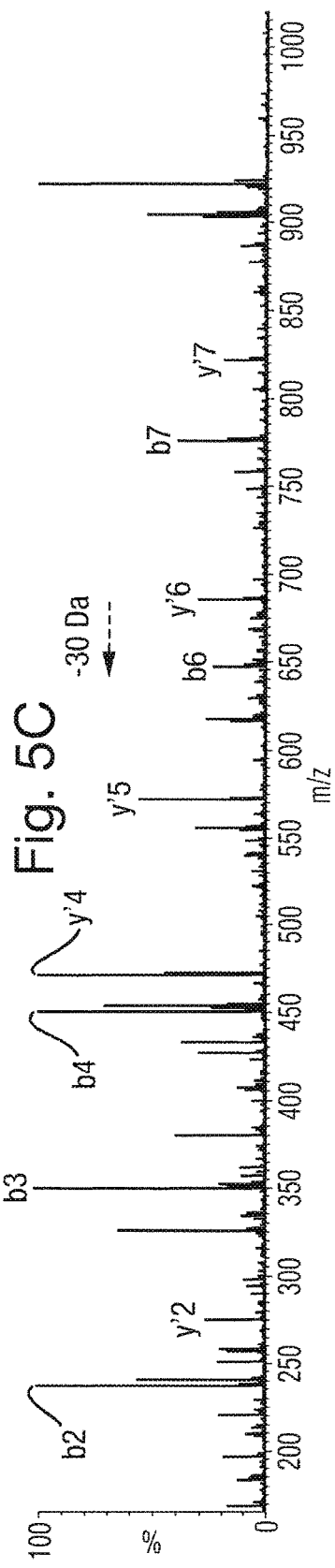

MASS SPECTROMETRY FOR DETERMINING IF A MUTATED VARIANT OF A TARGET PROTEIN IS PRESENT IN A SAMPLE

CROSS-REFERENCE TO RELATED APPLICATION APPLICATIONS

This application represents the U.S. National Phase of International Application number PCT/GB2015/052881 entitled "Mass Spectrometry for Determining if a Mutated Variant of a Target Protein is Present in a Sample" filed 1 Oct. 2015, which claims priority from and the benefit of United Kingdom patent application No. 1417387.6 filed on 1 Oct. 2014. The entire contents of this application are incorporated herein by reference.

FIELD OF THE INVENTION

The present invention relates generally to a method of mass spectrometry and a mass spectrometer, and in particular to methods and spectrometers for detecting mutated variants of proteins such as mutated haemoglobin proteins.

BACKGROUND

Current human haemoglobinopathy hospital screening programs rely on analysing whole blood using phenotypic methods such as cation-exchange High Performance Liquid Chromatography ("HPLC") or iso-electric focusing. These methods provide presumptive variant identification but they do not positively identify any variant or identify novel variants. The specificity of separation is not sufficient for precise identification of a wide range of haemoglobin variants that exist in the current patient population. Definitive identification usually requires protein sequencing using mass spectrometry or DNA analysis. DNA analysis is much slower compared to mass spectrometry, relatively costly and requires a high degree of scientific expertise.

Mass spectrometry using Electrospray Ionisation ("ESI"), with or without HPLC, followed by Collision Induced Dissociation ("CID") and MS/MS analysis of tryptically digested blood samples is known to be an effective method for precise identification. However, the digestion and mass spectral analysis still require at least 30 minutes per sample analysis.

These problems also exist in non-human haemoglobinopathy as well as with analysing proteins other than haemoglobin.

It is desired to provide an improved method of mass spectrometry and an improved mass spectrometer.

SUMMARY OF THE PRESENT INVENTION

According to a first aspect, the present invention provides a method of mass spectrometry for determining if a mutated variant of a target protein is present in a sample, comprising:

introducing said sample comprising the target protein into a mass spectrometer;

subjecting the sample to fragmentation so as to cause said target protein to fragment to form first fragment ions;

fragmenting said first fragment ions to form second fragment ions;

mass analysing said second fragment ions to obtain first spectral data; and determining that an ion in the first spectral data has a mass to charge ratio that differs from the mass to charge ratio of an ion that would be observed if said target protein was a normal unmutated version of said target protein, and by an amount that corresponds to a mass difference that would be caused by the target protein being a mutated variant of said target protein.

When said determining step is fulfilled, the method considers that said ion in the spectral data is from a mutated variant of said target protein. This method provides a fast and efficient manner of identifying whether or not a mutated variant of a known target protein is present in the sample. This may be useful, for example, in determining that a sample is from a diseased organism.

The second fragment ions described herein may be first generation fragment ions of the first fragment ions, i.e. daughter ions of the first fragment ions. Alternatively, the second fragment ions may be second or further generation fragment ions of the first fragment ions, i.e. granddaughter ions or further generation fragment ions of the first fragment ions.

The mutated variant of said target protein may correspond to a normal unmutated version of the target protein in which an amino-acid has mutated or has been substituted by another amino-acid.

The method may compare the first spectral data to corresponding data for a non-mutated version of the target protein (e.g. library data), in order to determine that the ion in the first spectral data has a mass to charge ratio that differs from the mass to charge ratio of an ion that would be observed if said target protein was a normal unmutated version of said target protein. It may be determined that the mass difference corresponds to a mass difference that would be caused by the target protein being a mutated variant of said target protein, if the mass difference is equivalent to the mass difference that would be caused by a mutation of an amino-acid in the normal target protein to another type of amino-acid.

The sample may be, or may comprise: blood; whole-blood; diluted blood; or diluted whole blood; and/or the target protein may be haemoglobin or a haemoglobin beta chain.

The blood may be from an organism such as a human or animal.

The diluted blood may be blood diluted with water or another liquid. For example, the diluted blood may be diluted whole blood.

The target protein may be subjected to ionisation prior to said fragmentation step such that target protein ions are fragmented to form the first fragment ions; and optionally the target protein may be ionised in an ion source to form the target protein ions.

The sample may be electro-sprayed into the ion source and then ionised.

Said fragmentation may be Atmospheric Pressure Electron Capture Dissociation ('Ap-ECD'); Atmospheric Pressure Electron Transfer Dissociation ('Ap-ETD'); Electron Capture Dissociation ("ECD"); or Electron Transfer Dissociation ("ETD").

These fragmentation techniques enable rapid and effective analysis of proteins, although another fragmentation technique may be used.

The sample may be introduced directly into the mass spectrometer.

The sample may not be subjected to liquid chromatography.

The sample may be ionised in the mass spectrometer and the sample may not be subjected to separation or digestion prior to ionisation and/or fragmentation.

Said step of fragmenting said first fragment ions may comprise isolating one of said first fragment ions from the other fragment ions and then fragmenting the isolated ions so as to form the second fragment ions.

An ion filter may be used to perform said step of isolating ions, and the ion filter may be set to isolate ions having a mass to charge ratio or ion mobility corresponding to that of a first fragment ion from a non-normal mutated variant of the target protein.

Said target protein may be a haemoglobin protein; and the first fragment ion that is isolated and fragmented to form said second fragment ions may be a c8 fragment ion derived from a haemoglobin beta chain.

The ion filter may be set to isolate ions having a mass to charge ratio or ion mobility corresponding to a c8 ion from a non-normal mutated variant of a haemoglobin beta chain (i.e. from a mutated variant of the target protein). The ion filter may be set to isolate first fragment ions having a mass difference to that of a c8 ion from normal non-mutated variant of a haemoglobin beta chain. The mass difference may be 30 Da, or the mass difference may corresponds to a mutation of Glutamic Acid to Valine. This mass difference may be used to screen for sickle cell disease. However, other amino-acid mutations may be considered for detecting other clinically significant diseases. For example, mass differences corresponding to a mutation from Glu to Lys (mild anaemia, thalassemia minor or mild microcytosis) may be screened for, or a mass differences corresponding to a mutation from Glu to Gln (mild anaemia) may be screened for.

The step of fragmenting said first fragment ions may comprise fragmenting said first fragment ions using Collision Induced Dissociation ("CID"); and/or the isolated ions may be fragmented using CID. However, alternative fragmentation techniques may be used. A fragmentation technique other than CID, ECD and ETD may be used.

The method described herein may comprise determining from the first spectral data if an ion is present at a mass to charge ratio corresponding to the mass to charge ratio that an ion would be detected at only if the target protein (e.g. haemoglobin) in the sample was of a non-normal mutated variant.

The method may only consider (e.g. search for) mass differences that would be caused by amino-acid mutations/substitutions that are practically and/or theoretically possible in said ion in the first spectral data, i.e. mass differences that would be caused by mutations/substitutions that are possible in the target protein (e.g. haemoglobin).

The mass difference may be 30 Da; and/or the mass difference may correspond to a mutation of Glutamic Acid to Valine; and/or the mass difference may be a mass difference that would arise if the haemoglobin in the blood sample was from a patient having sickle cell disease. However, other mass differences may be searched for. For example, mass differences corresponding to a mutation from Glu to Lys (mild anaemia, thalassemia minor or mild microcytosis) may be screened for, or mass differences corresponding to a mutation from Glu to Gln (mild anaemia) may be screened for.

If or when an ion having said mass difference is detected, the ion may be considered and/or indicated as being from a non-normal mutated variant of the target protein (e.g. haemoglobin). For example, the ion may be considered and/or indicated as being from a non-normal mutated variant haemoglobin. The sample may be considered and/or indicated as potentially being from a patient having sickle cell disease.

The method may comprise using the mass to charge ratio of said ion in the first spectral data to identify the location of the mutation within the protein sequence of the target protein.

The mass to charge ratio of said ion in the first spectral data may be used to identify the position in the protein sequence at which the mutation has occurred. For example, the mass to charge ratio indicates which second fragment ion (e.g. sequence ion) comprises the mutation. This in turn may indicate the position in the parent or grandparent protein that the mutation has occurred at. Any of this positional data may be used to help identify the significance of the mutation.

For example, if the target protein is a haemoglobin protein, the mass to charge ratio of said ion in the first spectral data may indicate that the mutation is present in the b6 sequence ion (second generation fragment ion). This location may indicate that the mutation may be of clinical significance in that the sample may be from a patient having sickle cell disease (if the mass difference represents a mutation from Glu to Val). Alternatively, the sample may be from a patient having mild anaemia (if the mass difference represents a mutation from Glu to Lys). Alternatively, the mass to charge ratio of said ion in the first spectral data may indicate that the mutation is present in the b26 sequence ion (second generation fragment ion). This location may indicate that the mutation may be of clinical significance in that the sample may be from a patient having thalassemia minor or microcytosis (if the mass difference represents a mutation from Glu to Lys). Alternatively, the mass to charge ratio of said ion in the first spectral data may indicate that the mutation is present in the b121 sequence ion (second generation fragment ion). This location may indicate that the mutation may be of clinical significance in that the sample may be from a patient having mild anaemia (if the mass difference represents a mutation from either Glu to Lys, or from Glu to Lys).

The method may comprise using the value of said mass difference to identify the type of mutation in the sequence of the target protein.

The mass difference may be equivalent to the mass difference between two different amino-acids.

The mass difference may correspond to a mass difference that would be caused by different amino-acid mutations. In this case, the method may only consider amino-acid mutations that would be practically or theoretically possible at the identified location of the mutation. The identified location and mass difference may therefore be used to identify the type of mutation that has occurred.

The method may comprise, for example, identifying, from the location and type of mutation, that the sample was taken from a patient having sickle cell disease.

The method may comprise identifying the type of variant of the target protein in the sample, or identifying a disease in the sample, from the location and/or type of mutation.

The method may comprise analysing the target protein in a precursor ion mode without it first being fragmented. If said ion having said mass difference is detected in the first spectral data, a related precursor ion detected in said precursor ion mode may be considered and/or indicated as being a mutated precursor ion from a non-normal mutated variant of the target protein. The method may then determine whether or not the precursor ions contain a precursor ion corresponding to an unmutated version of the mutated precursor ion. If the method determines that the precursor ions contain both said mutated precursor ion and said unmutated version of the precursor ion, then the variant may be determined to be a heterozygous variant. Alternatively, if the method determines that the precursor ions contain said mutated precursor ion and not said unmutated version of the precursor ion, then the variant may be determined to be a homozygous variant.

The method may comprise comparing the intensity of said ion in the first spectral data to a first threshold value, and determining that the variant is a homogeneous variant if the intensity is above the first threshold value; and/or comparing the intensity of said ion in the first spectral data to a second threshold value, and determining that the variant is a heterogeneous variant if the intensity is below the second threshold value.

If said ion having said mass difference is detected in the first spectral data, the first fragment ion that is fragmented to produce the second spectral data may be considered and/or indicated as being a mutated first fragment ion from a non-normal mutated variant of the target protein; and the method may determine whether or not the first fragment ions contain a fragment ion corresponding to an unmutated version of the mutated first fragment ion. If the method determines that the first fragment ions contain both said mutated first fragment ion and said unmutated version of the mutated first fragment ion, then the variant may be determined to be a heterozygous variant. If the method determines that the first fragment ions contain said mutated first fragment ion and not said unmutated version of the mutated first fragment ion, then the variant may be determined to be a homozygous variant For example, if the target protein is haemoglobin and the first fragment ions are determined to contain the mutated c8 ion and the unmutated c8 ion from the haemoglobin beta chain, then it may be considered that the variant is heterozygous. If the first fragment ions are determined to contain the mutated c8 ion and not the unmutated c8 ion from the haemoglobin beta chain, then it may be considered that the variant is homozygous The unmutated version of the mutated first fragment ion may be determined to be present if a first fragment ion is present or detected that has a mass to charge ratio corresponding to that of the mutated first fragment ion plus or minus said mass difference determined to have been caused by the mutation detected in the second fragment ions.

The presence or absence of said unmutated first fragment ion may be determined directly by mass analysing the first fragment ions. Additionally, or alternatively, the presence or absence of said unmutated first fragment ion may be determined indirectly by setting an ion filter so as to transmit only ions having a mass to charge ratio or ion mobility of the unmutated first fragment ion into the fragmentation region that generates the second fragment ions. If no second fragment ions are detected from this then the unmutated first fragment ion may be determined not to be present. Conversely, if second fragment ions are detected from this then the unmutated first fragment ion may be determined to be present.

The method may comprise a further mode that determines if ions in the first spectral data are at mass to charge ratios corresponding to the mass to charge ratios that the ions would be detected at if the target protein (e.g. haemoglobin) in the sample was normal. This may be achieved by comparing the experimental data to a library of corresponding spectral data for the normal target protein. The method may further comprise providing an indication that the target protein (e.g. haemoglobin) in the sample is normal and unmutated if the ions in the first spectral data are at mass to charge ratios corresponding to the mass to charge ratios that the ions would be detected at if the target protein (e.g. haemoglobin) in the sample was normal and unmutated.

The method may comprise a further mode for putative identification of variants, e.g. based on analysis of the first fragment ions. The method may comprise mass analysing said first fragment ions to obtain second spectral data; and determining whether or not ions in the second spectral data are at mass to charge ratios corresponding to the mass to charge ratios that these ions would be detected at if the target protein in the sample was a normal, unmutated target protein. The method may optionally further comprise providing an indication that the target protein in the sample is a normal unmutated target protein if the ions in the second spectral data are at mass to charge ratios corresponding to the mass to charge ratios that the ions would be detected at if the target protein in the sample was a normal unmutated target protein.

The method may comprise mass analysing said first fragment ions to obtain second spectral data; and determining from the second spectral data if an ion is present at a mass to charge ratio corresponding to the mass to charge ratio that an ion would be detected at only if the target protein in the sample was of a mutated non-normal variant.

The method may comprise determining that an ion in the second spectral data has a mass to charge ratio that differs from the mass to charge ratio of an ion that would be observed if a normal unmutated target protein had been analysed, and by an amount that corresponds to a mass difference that would be caused by the analysed target protein being a non-normal mutated variant of the target protein or that would be caused by a mutation/substitution of an amino-acid of the normal target protein for another amino-acid.

The method may only consider (e.g. search for) mass differences that would be caused by amino-acid mutations/substitutions that are practically and/or theoretically possible in said ion in the second spectral data.

The target protein described herein may be haemoglobin, or a haemoglobin beta chain.

The mass difference may be 30 Da and/or the mass difference may correspond to a mutation of Glutamic Acid to Valine. Alternatively, or additionally, the mass difference may be a mass difference that would arise if the haemoglobin in the blood sample was from a patient having sickle cell disease.

If an ion having said mass difference is detected, the method may further comprise providing an indication that the target protein in the sample is a non-normal mutated variant.

The method may determine if a particular first fragment ion derived from the target protein is present at a mass to charge ratio corresponding to that expected for normal unmutated target protein; and/or if a particular first fragment ion derived from a target protein is present at a mass to charge ratio corresponding to that expected for a non-normal mutated variant of the target protein.

If the target protein is haemoglobin, or a haemoglobin beta chain, the method may determine if a c8 fragment ion derived from a haemoglobin beta chain has a mass to charge ratio corresponding to that expected for normal unmutated haemoglobin; and/or the method may determine if a c8 fragment ion derived from a haemoglobin beta chain has a mass to charge ratio corresponding to that expected for a non-normal mutated variant of haemoglobin.

The first aspect of the present invention also provides a mass spectrometer for determining if a mutated variant of a target protein is present in a sample, the spectrometer comprising:

a device arranged and configured to receive said sample comprising the target protein;

at least one fragmentation device;

a mass analyser;

a processor; and a control system arranged and configured to:

subject the sample to fragmentation in the at least one fragmentation device so as to cause said target protein to fragment to form first fragment ions;

fragment said first fragment ions in said at least one fragmentation device so as to form second fragment ions;

mass analyse said second fragment ions in said mass analyser so as to obtain first spectral data; and control the processor to determine that an ion in the first spectral data has a mass to charge ratio that differs from the mass to charge ratio of an ion that would be observed if said target protein was a normal unmutated version of said target protein, and by an amount that corresponds to a mass difference that would be caused by the target protein being a mutated variant of said target protein.

The spectrometer may be arranged and configured to perform any of the methods described herein.

From a second aspect, the present invention provides a method of mass spectrometry comprising:

introducing a blood sample into a mass spectrometer system; and using Electron Capture Dissociation ("ECD") or Electron Transfer Dissociation ("ETD") to subject said sample to fragmentation so as to cause haemoglobin proteins to fragment to form first fragment ions.

This method provides a rapid and effective manner of analysing haemoglobin proteins.

The ECD may be Atmospheric Pressure Electron Capture Dissociation ('Ap-ECD'); and said ETD may be Atmospheric Pressure Electron Transfer Dissociation ('Ap-ETD').

The step of introducing the blood sample into the mass spectrometer system may comprise introducing the blood sample directly into the mass spectrometer system.

The blood sample may not be subjected to liquid chromatography.

The blood sample may be ionised in the mass spectrometer system, but with the blood sample not being subjected to separation or digestion prior to ionisation.

The blood sample introduced into the mass spectrometer system may be, or may comprise, whole blood; and/or said blood sample may comprise, or may be, a diluted blood sample.

The diluted blood sample may be a blood sample diluted with water or another liquid. For example, the diluted blood sample may be diluted whole blood.

The step of using ECD or ETD to subject said sample to fragmentation may comprise using said ECD or ETD to subject said sample to in-source fragmentation so as to cause the haemoglobin proteins to fragment to form the first fragment ions.

The method may comprise delivering the blood sample to an ion source and ionising the blood sample, or components thereof, to form haemoglobin protein ions, and then using said ECD or ETD to fragment said haemoglobin protein ions to form said first fragment ions. The haemoglobin protein ions may be fragmented in said ion source by said ECD or ETD.

It has been found that Ap-ECD and Ap-ETD, particularly in-source Ap-ECD and Ap-ETD, are especially effective ways to fragment the proteins for analysis.

The blood sample may be electro-sprayed into an, or the, ion source and then ionised.

The method may comprise mass analysing said first fragment ions to obtain first spectral data; and determining whether or not ions in the first spectral data are at mass to charge ratios corresponding to the mass to charge ratios that these ions would be detected at if the haemoglobin in the blood sample was normal, unmutated haemoglobin. The method may further comprise providing an indication that the haemoglobin in the blood sample is normal unmutated haemoglobin if the ions in the first spectral data are at mass to charge ratios corresponding to the mass to charge ratios that the ions would be detected at if the haemoglobin in the blood sample was normal unmutated haemoglobin.

The method may comprise mass analysing said first fragment ions to obtain first spectral data; and determining from the first spectral data if an ion is present at a mass to charge ratio corresponding to the mass to charge ratio that an ion would be detected at only if the haemoglobin in the blood sample was of a mutated non-normal variant. The method may further comprise providing an indication that the haemoglobin in the blood sample is a mutated variant of haemoglobin.

The method may comprise determining that an ion in the first spectral data has a mass to charge ratio that differs from the mass to charge ratio of an ion that would be observed if normal unmutated haemoglobin had been analysed, and by an amount that corresponds to a mass difference that would be caused by the analysed haemoglobin being a non-normal variant or that would be caused by a mutation/substitution of an amino-acid of normal haemoglobin for another amino-acid.

The method may only consider (e.g. search for) mass differences that would be caused by amino-acid mutations/substitutions that are practically and/or theoretically possible in said ion in the first spectral data (e.g. mass differences that would be caused by mutations/substitutions that are possible in the haemoglobin beta chain).

The mass difference may be 30 Da; and/or the mass difference may correspond to a mutation of Glutamic Acid to Valine; and/or the mass difference may be a mass difference that would arise if the haemoglobin in the blood sample was from a patient having sickle cell disease.

If an ion having said mass difference is detected, the method may further comprise providing an indication that the haemoglobin in the blood sample is a non-normal mutated variant and/or that the blood sample is potentially from a patient having sickle cell disease.

The method may determine if a particular first fragment ion derived from a haemoglobin beta chain is present at a mass to charge ratio corresponding to that expected for normal unmutated haemoglobin; and/or if a particular first fragment ion derived from a haemoglobin beta chain is present at a mass to charge ratio corresponding to that expected for a non-normal mutated variant of haemoglobin.

For example, the method may determine if a c8 fragment ion derived from a haemoglobin beta chain has a mass to charge ratio corresponding to that expected for normal unmutated haemoglobin; and/or if a c8 fragment ion derived from a haemoglobin beta chain has a mass to charge ratio corresponding to that expected for a non-normal mutated variant of haemoglobin.

The method may comprise fragmenting at least some of said first fragment ions to form second fragment ions.

The step of fragmenting at least some of said first fragment ions may comprise isolating one of said first fragment ions from the other fragment ions and then fragmenting the isolated ions so as to form the second fragment ions.

An ion filter may be used to perform said step of isolating ions, and the ion filter may be set to isolate ions having a mass to charge ratio or ion mobility corresponding to that of an ECD or ETD fragment ion from a normal unmutated haemoglobin beta chain. Alternatively, an ion filter may be used to perform said step of isolating ions, and the ion filter may be set to isolate ions having a mass to charge ratio or ion mobility corresponding to that of an ECD or ETD fragment ion from a non-normal mutated variant of a haemoglobin beta chain.

The first fragment ion that is isolated and fragmented to form said second fragment ions is a c8 fragment ion derived from a haemoglobin beta chain.

The ion filter may be set to isolate ions having a mass to charge ratio or ion mobility corresponding to a c8 ion from a non-normal mutated variant of a haemoglobin beta chain. The ion filter may be set to isolate ions having mass difference to that of a c8 ion from a normal non-mutated variant of a haemoglobin beta chain; wherein the mass difference is 30 Da, or wherein the mass difference corresponds to a mutation of Glutamic Acid to Valine.

Alternatively, or in a subsequent experiment, the ion filter may be set to isolate ions having a mass to charge ratio or ion mobility corresponding to a c8 ion from a normal unmutated haemoglobin beta chain.

The step of fragmenting at least some of said first fragment ions may comprise fragmenting at least some of said first fragment ions using Collision Induced Dissociation ("CID"); and/or wherein the isolated ions are fragmented using CID. However, alternative fragmentation techniques may be used. A fragmentation technique other than CID, ECD and ETD may be used.

The method may comprise mass analysing the second fragment ions to obtain second spectral data; and determining if ions in the second spectral data are at mass to charge ratios corresponding to the mass to charge ratios that the ions would be detected at if the haemoglobin in the blood sample was normal. This may be achieved by comparing the experimental data to a library of corresponding spectral data for normal haemoglobin. The method may further comprise providing an indication that the haemoglobin in the blood sample is normal and unmutated if the ions in the second spectral data are at mass to charge ratios corresponding to the mass to charge ratios that the ions would be detected at if the haemoglobin in the blood sample was normal and unmutated.

The method may comprise mass analysing the second fragment ions to obtain second spectral data; and determining from the second spectral data if an ion is present at a mass to charge ratio corresponding to the mass to charge ratio that an ion would be detected at only if the haemoglobin in the blood sample was of a non-normal mutated variant.

The method may comprise determining that an ion in the second spectral data has a mass to charge ratio that differs from the mass to charge ratio of an ion that would be observed if normal unmutated haemoglobin had been analysed, and by an amount that corresponds to a mass difference that would be caused by the analysed haemoglobin being a non-normal variant or that would be caused by a mutation/substitution of an amino-acid of normal haemoglobin for another amino-acid.

The method may only consider (e.g. search for) mass differences that would be caused by amino-acid mutations/substitutions that are practically and/or theoretically possible in said ion in the second spectral data (e.g. mass differences that would be caused by mutations/substitutions that are possible in the haemoglobin beta chain.

The mass difference may be 30 Da; and/or the mass difference may correspond to a mutation of Glutamic Acid to Valine; and/or the mass difference may be a mass difference that would arise if the haemoglobin in the blood sample was from a patient having sickle cell disease. Other mass differences may be searched for to screen for other diseases, e.g. as described above in relation to the first aspect of the invention.

If an ion having said mass difference is detected, the ion may be considered and/or indicated as being from a non-normal mutated variant of haemoglobin. For example, the blood sample may be considered and/or indicated as potentially being from a patient having sickle cell disease.

The method may comprise using the value of said mass difference to identify the type of mutation in the haemoglobin sequence.

This may be used to identify the type of amino-acid mutation. The mass difference may correspond to a mass difference that would be caused by more than one type of amino-acid mutation. In this case, the method may only consider amino-acid mutations that would be practically or theoretically possible in the protein or at the identified location of the mutation. The identified location and mass difference may therefore be used to identify the type of mutation that has occurred.

The method may comprise using the mass to charge ratio of said ion in the second spectral data to identify the location of the mutation within the haemoglobin sequence.

The mass to charge ratio of said ion in the second spectral data may be used to identify the position in the protein sequence at which the mutation has occurred. For example, the mass to charge ratio indicates which second generation fragment ion (e.g. sequence ion) comprises the mutation. This in turn may indicate the position in the parent or grandparent protein that the mutation has occurred at. Any of this positional data may be used to help identify the significance of the mutation.

For example, the mass to charge ratio of said ion in the second spectral data may indicate that the mutation is present in the b6 sequence ion (second generation fragment ion). This location may indicate that the mutation may be of clinical significance in that the sample may be from a patient having sickle cell disease (if the mass difference represents a mutation from Glu to Val). Alternatively, the sample may be from a patient having mild anaemia (if the mass difference represents a mutation from Glu to Lys). Alternatively, the mass to charge ratio of said ion in the first spectral data may indicate that the mutation is present in the b26 sequence ion (second generation fragment ion). This location may indicate that the mutation may be of clinical significance in that the sample may be from a patient having thalassemia minor or microcytosis (if the mass difference represents a mutation from Glu to Lys). Alternatively, the mass to charge ratio of said ion in the first spectral data may indicate that the mutation is present in the b121 sequence ion (second generation fragment ion). This location may indicate that the mutation may be of clinical significance in that the sample may be from a patient having mild anaemia (if the mass difference represents a mutation from either Glu to Lys, or from Glu to Lys).

The method may comprise identifying a type of haemoglobin variant in the blood sample or a blood disease in the blood sample from the location and/or type of mutation; and/or identifying from the location and type of mutation that the blood sample was taken from a patient having sickle cell disease.

The method may comprise analysing the blood sample in a precursor ion mode without prior fragmentation. If said ion having said mass difference is detected, a related precursor ion detected in said precursor ion mode may be considered and/or indicated as being a mutated precursor ion from a non-normal mutated variant of haemoglobin. The method may then determine whether or not the precursor ions contain a precursor ion corresponding to an unmutated version of the mutated precursor ion. If the method determines that the precursor ions contain both said mutated precursor ion and said unmutated version of the precursor ion, then the variant is determined to be a heterozygous variant. Alternatively, if the method determines that the precursor ions contain said mutated precursor ion and not said unmutated version of the precursor ion, then the variant is determined to be a homozygous variant.

The method may comprise comparing the intensity of said ion in the second spectral data to a first threshold value, and determining that the haemoglobin variant is a homogeneous variant if the intensity is above the first threshold value; and/or comparing the intensity of said ion in the second spectral data to a second threshold value, and determining that the haemoglobin variant is a heterogeneous variant if the intensity is below the second threshold value.

If said ion having said mass difference is detected, the first fragment ion that is fragmented to produce the second spectral data may be considered and/or indicated as being a mutated first fragment ion from a non-normal mutated variant of haemoglobin; and the method may determine whether or not the first fragment ions contain a fragment ion corresponding to an unmutated version of the mutated first fragment ion. If the method determines that the first fragment ions contain both said mutated first fragment ion and said unmutated version of the mutated first fragment ion, then the haemoglobin variant may be determined to be a heterozygous variant. If the method determines that the first fragment ions contain said mutated first fragment ion and not said unmutated version of the mutated first fragment ion, then the haemoglobin variant may be determined to be a homozygous variant For example, if the first fragment ions are determined to contain the mutated c8 ion and the unmutated c8 ion from the haemoglobin beta chain, then it may be considered that the variant is heterozygous. If the first fragment ions are determined to contain the mutated c8 ion and not the unmutated c8 ion from the haemoglobin beta chain, then it may be considered that the variant is homozygous The unmutated version of the mutated first fragment ion may be determined to be present if a first fragment ion is present or detected that has a mass to charge ratio corresponding to that of the mutated first fragment ion plus or minus said mass difference determined to have been caused by the mutation detected in the second fragment ions.

The presence or absence of said unmutated first fragment ion may be determined directly by mass analysing the first fragment ions. Additionally, or alternatively, the presence or absence of said unmutated first fragment ion may be determined indirectly by setting an ion filter so as to transmit only ions having a mass to charge ratio or ion mobility of the unmutated first fragment ion into the fragmentation region that generates the second fragment ions. If no second fragment ions are detected from this then the unmutated first fragment ion may be determined not to be present. Conversely, if second fragment ions are detected from this then the unmutated first fragment ion may be determined to be present.

The fragmentation of the first fragment ions and/or the analysis of the second fragment ions may only be performed if the putative analysis of the first fragment ions in the first spectral data indicates that the haemoglobin is a mutated variant.

The method may comprise using said first fragment ions and/or said second fragment ions to identify the location of haemoglobin sequence mutations.

The present invention also provides a method of identifying a type of haemoglobin variant in a blood sample or a blood disease in a blood sample comprising a method as described herein.

The second aspect of the present invention also provides a mass spectrometer comprising:

a device arranged and adapted to receive a blood sample;

an Electron Capture Dissociation ("ECD") device or an Electron Transfer Dissociation ("ETD") device; and a control system arranged and adapted:

(i) to subject said sample to fragmentation using said ECD device or said ETD device so as to cause haemoglobin proteins to fragment to form first fragment ions.

The spectrometer may be arranged and configured to perform any of the methods described herein, e.g. in relation to the second aspect of the present invention.

For example, the control system may be arranged and adapted to subject said sample to in-source fragmentation.

The ECD device may be an Ap-ECD device and the ETD device may be an Ap-ETD device.

The blood sample may comprise a diluted blood sample.

The spectrometer may further comprise a fragmentation device arranged and adapted to fragment at least some of said first fragment ions to form second fragment ions.

The fragmentation device may comprises a Collision Induced Dissociation ("CID") fragmentation device.

The control system may be arranged and adapted to use the first fragment ions and/or the second fragment ions to identify the location of haemoglobin sequence mutations.

The present invention also provides a method of mass spectrometry comprising:

introducing a blood sample directly into a mass spectrometer system; and using Atmospheric Pressure Electron Capture Dissociation ("Ap-ECD") or Atmospheric Pressure Electron Transfer Dissociation ("Ap-ETD") to subject said sample to in-source fragmentation so as to cause haemoglobin proteins to fragment to form first fragment ions;

fragmenting at least some of said first fragment ions to form second fragment ions; and using said first fragment ions and/or said second fragment ions to identify the location of haemoglobin sequence mutations.

The step of fragmenting said at least some of the first fragment ions may comprise fragmenting at least some of said first fragment ions using Collision Induced Dissociation ("CID").

The spectrometer may comprise an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source.

The spectrometer may comprise one or more continuous or pulsed ion sources.

The spectrometer may comprise one or more ion guides.

The spectrometer may comprise one or more ion mobility separation devices and/or one or more Field Asymmetric Ion Mobility Spectrometer devices.

The spectrometer may comprise one or more ion traps or one or more ion trapping regions.

The spectrometer may comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

The spectrometer may comprise one or more energy analysers or electrostatic energy analysers.

The spectrometer may comprise one or more ion detectors. The spectrometer may comprise one or more mass filters selected from the group consisting of:
(i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The spectrometer may comprise a device or ion gate for pulsing ions; and/or
a device for converting a substantially continuous ion beam into a pulsed ion beam.

The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The spectrometer may comprise a chromatography or other separation device upstream of an ion source. The chromatography separation device may comprise a liquid chromatography or gas chromatography device. Alternatively, the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

A chromatography detector may be provided, wherein the chromatography detector comprises either:

a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or a non-destructive chromatography detector optionally selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

Embodiments of the present invention provide a fast (non-HPLC) and accurate method and/or apparatus for determining haemoglobin variants directly from diluted whole blood samples. An atmospheric pressure Electron Capture Dissociation source ("Ap-ECD") may be used to generate Electron Capture Dissociation ("ECD") fragments. ECD fragment or daughter ions may then be further subjected to MS/MS by Collision Induced Dissociation ("CID") in order to confirm sequence of variants.

According to the methods described herein, a first fragment ion may be selected for fragmentation by a quadrupole (or ion mobility device), and then fragmented to form the second fragment ions. The sequence variant ions determined by MS/MS may be measured by processing full spectrum scanning data or by single ion monitoring and their levels quantified.

The method described herein may operate as a pseudo-MS$^3$ method.

BRIEF DESCRIPTION OF THE DRAWINGS

Various embodiments of the present invention will now be described, by way of example only, and with reference to the accompanying drawings in which:

FIGS. 5A-5C show fragment ion spectra for blood samples containing normal (AA), heterozygote (AS) and homozygote (SS) variants of haemoglobin, obtained by CID dissociation of a fragment ion observed in FIGS. 3A-3C.

DETAILED DESCRIPTION

Figure 1:
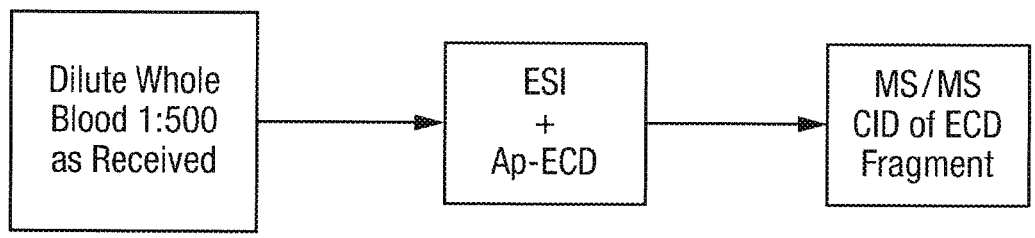
FIG. 1 shows a simplified workflow according to an embodiment of the present invention.

A simplified workflow according to an embodiment of the present invention is shown in FIG. 1. The workflow comprises diluting the blood sample taken from a patient and introducing the diluted blood sample directly into a mass spectrometer. The ratio of dilution of blood to water in this example is 1:500, although other dilutions may of course be used. Components or molecules in the diluted blood sample are then ionised within the mass spectrometer. In a first mode, the resulting ions are then subjected to Atmospheric Pressure Electron Capture Dissociation ("Ap-ECD"), or Atmospheric Pressure Electron Transfer Dissociation ("Ap-ETD"), so as to dissociate the ions to form first fragment ions, e.g. to dissociate ions derived from haemoglobin proteins to form first fragment ions. The resulting spectra may be used to putatively determine the location of a mutation, as will be described further below in relation to FIGS. 3A-3C.

In a second mode, MS/MS analysis may be performed. This may be performed by selectively transmitting a first fragment ion having a particular mass to charge ratio (or range of mass to charge ratios) and then fragmenting that ion by Collisionally Induced Dissociation (CID). The resulting spectra may be used to accurately determine the location of a mutation, as will be described further below in relation to FIGS. 5A-5C.

The above-described workflow does not involve the relatively time consuming steps of HPLC and sample digestion, and does not require complex workflows. The simplified workflow is relatively fast, only requiring approximately a minute or less per stage. Furthermore, the procedure may be performed using a small, low-cost bench-top instrument.

Figure 2A:
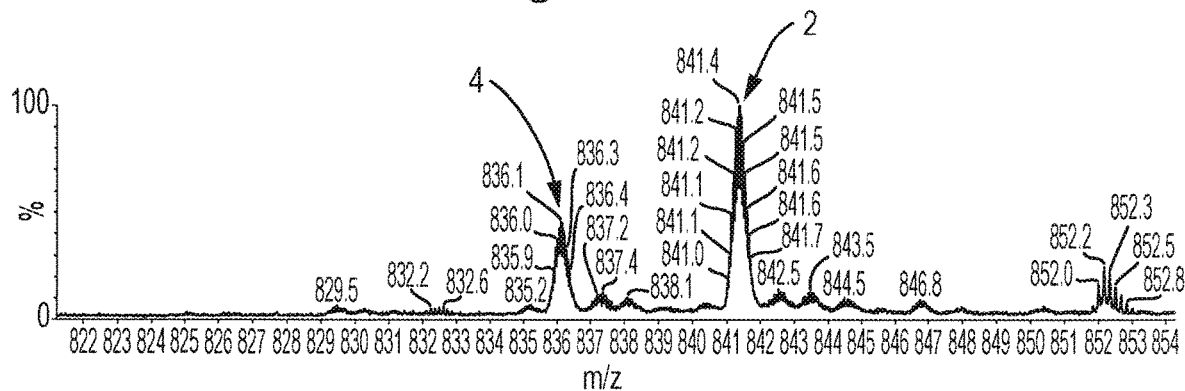
FIGS. 2A-2C show MS precursor ion spectra for blood samples containing normal (AA), heterozygote (AS) and homozygote (SS) variants of haemoglobin.
Figure 2B:
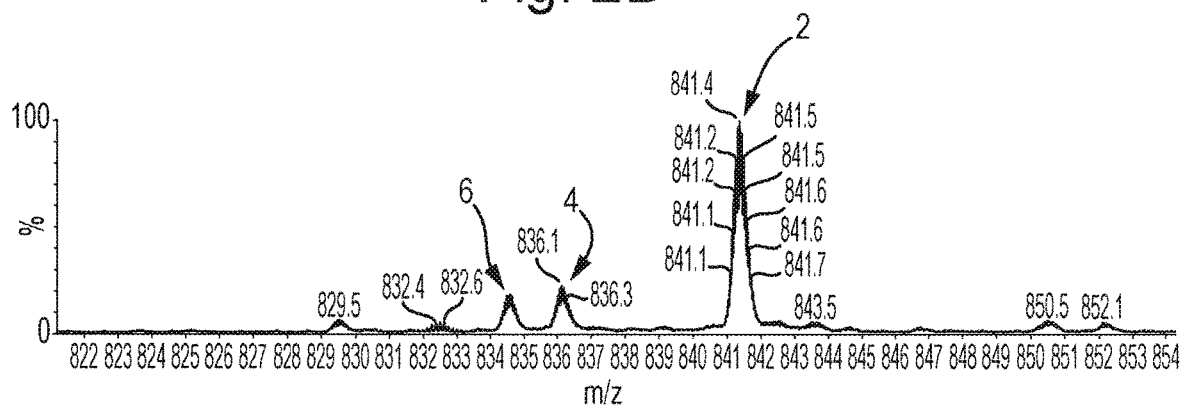
Figure 2C:
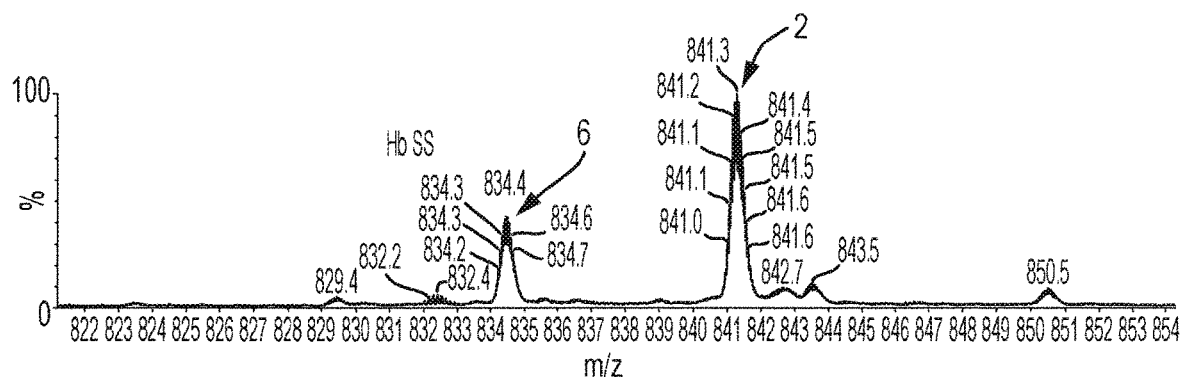

FIGS. 2A-2C show MS spectra for precursor ions from three different blood samples. FIG. 2A shows an MS spectra for ions from a normal (AA) blood sample. The most intense peak 2 shown in the spectrum is due to ions from the alpha chain (ions having a charge state of 18+ and having an average molecular weight of 15126 Da) and the second most intense peak 4 is due to beta chain ions (ions having a charge state of 19+ and having an average molecular weight of 15867 Da). As the blood sample is a normal sample (AA), both beta chains are unmodified and appear at the same mass to charge ratio.

FIG. 2B shows an MS spectra for ions from a heterozygous (AS) blood sample, i.e. a sample in which one of the beta chains is mutated and one of the beta chains is not mutated. The spectrum shows an ion peak 2 due to the alpha chain and an ion peak 4 due to the non-mutated beta chain (beta A) at the same locations as the alpha and beta chain peaks in FIG. 2A. However, the non-mutated beta chain peak 4 in FIG. 2B has a lower intensity than that in FIG. 2A, because the blood sample analysed to produce FIG. 2B does not contain only non-mutated beta chains but also includes mutated beta chains. FIG. 2B shows an ion peak 6 corresponding to the mutated beta chain (beta S), which has an approximately similar intensity to peak 4 shown in FIG. 2B for the non-mutated beta chain (beta A). The ion peak 6 is due to ions having a charge state of 19+ and having an average molecular weight of 15837 Da.

FIG. 2C shows an MS spectra for ions from a homozygous (SS) blood sample, i.e. a sample in which both of the beta chains are mutated. The spectrum shows an ion peak 2 due to the alpha chain at substantially the same location and intensity as the alpha chain peaks in FIGS. 2A and 2B. The spectrum of FIG. 2C includes only a single beta chain peak 6 that is located at the same location as the mutated beta chain (beta S) peak shown in FIG. 2B. The beta chain peak 6 in FIG. 2C has a higher intensity than that in FIG. 2B (and the substantially same intensity as the non-mutated beta chain 4 in FIG. 2A), because the blood sample analysed to produce FIG. 2C contains only mutated beta chains and no non-mutated beta chains. The ion peak 6 in FIG. 2C is due to ions having a charge state of 19+ and having an average molecular weight of 15837 Da.

It can be seen by comparing FIGS. 2A-2C that the mutation in the beta chain in the AS and SS variants (FIGS. 2B and 2C) causes the beta chain to decrease in mass by 30 Da, as compared to an non-mutated beta chain (FIG. 2A). However, the location of the mutation has not been determined precisely and so is not directly indicative of whether the mutation is problematic or not (e.g. whether or not the mutation is symptomatic in the patient). It may therefore be desirable to use the technique described in relation to FIG. 1 to determine the location of the mutation more accurately.

Figure 3A:
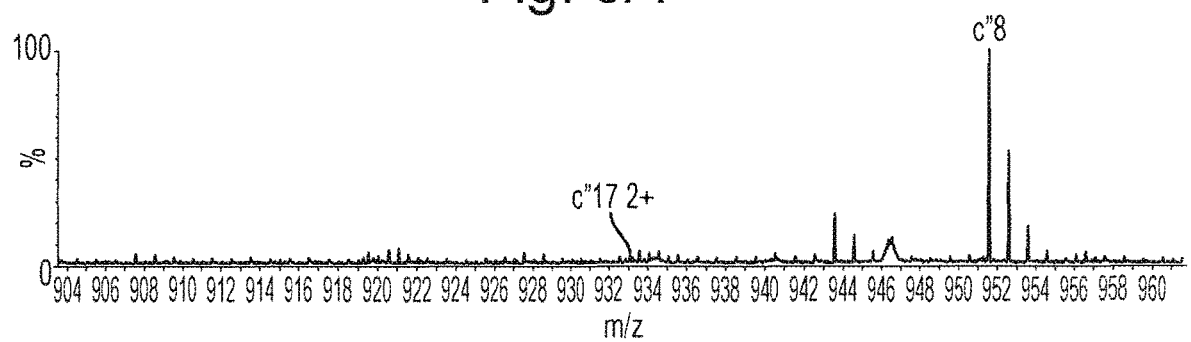
FIGS. 3A-3C show fragment ion spectra for blood samples containing normal (AA), heterozygote (AS) and homozygote (SS) variants of haemoglobin, obtained by switching on a UV lamp in an MS mode.
Figure 3B:
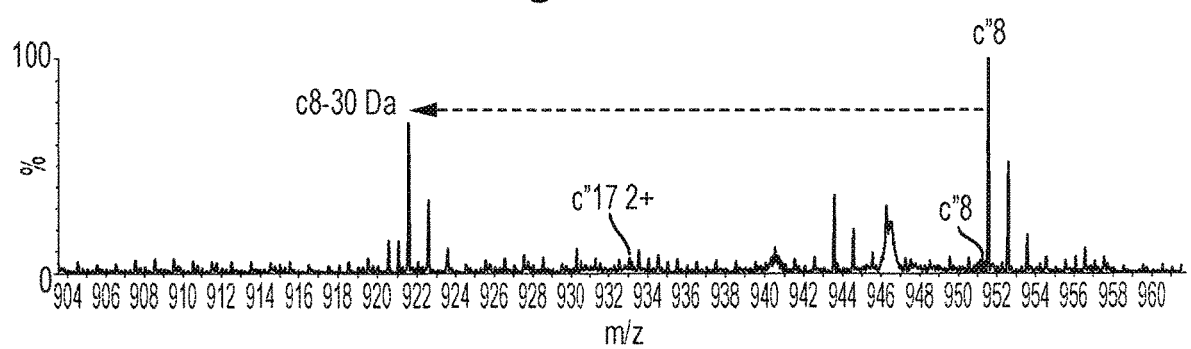
Figure 3C:
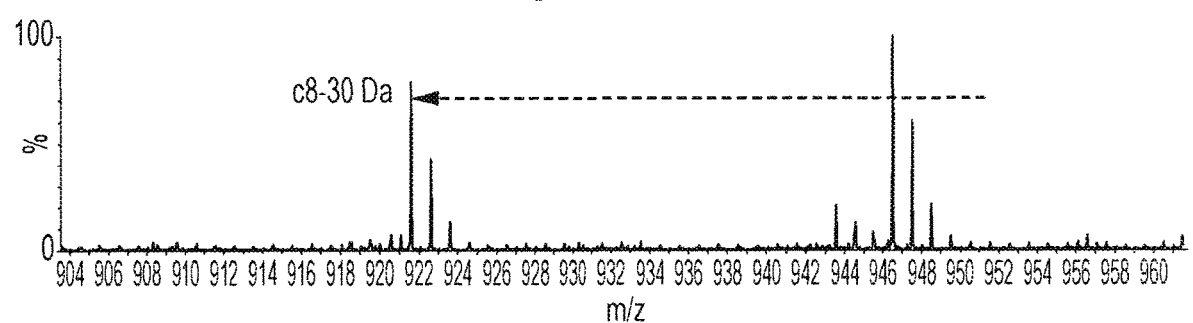

FIGS. 3A-3C show fragment ion spectra obtained for the three different blood samples analysed in FIGS. 2A-2C, respectively. The fragment ion spectra were obtained by switching on an Atmospheric Pressure Electron Capture Dissociation ("Ap-ECD") ultraviolet lamp whilst in a MS mode of operation. The light from the lamp may generate photoelectrons, e.g. via the ionization of a supplementary acetone flow within the ion source. The photoelectrons may then react with the multiply charged analyte ions, thereby generating Electron Capture Dissociation (ECD) type fragment ions. Several 'c' type fragment ions are generated.

FIG. 3A shows the spectrum for the normal (AA) blood sample. In this example, the c8 fragment ion has a mass to charge ratio of 952 and is derived from a normal beta chain (beta A). A c8 ion exists in only one form for the normal (AA) blood sample, at a mass to charge ratio of 952.

FIG. 3B shows the spectrum for the heterozygous (AS) blood sample. As in FIG. 3A, the spectrum shows a c8 fragment ion having a mass to charge ratio of 952, which is derived from a normal beta chain (beta A). The spectrum of FIG. 3B also shows a c8 fragment having a mass to charge ratio of 922 and which is derived from a mutated beta chain (beta S).

FIG. 3C shows the spectrum for the homozygous (SS) blood sample. The c8 fragment ion having a mass to charge ratio of 952 that is shown in FIGS. 3A and 3B is missing, because such a fragment would be derived from a normal beta chain (beta A), which is not present in the homozygous (SS) blood sample. However, the spectrum of FIG. 3C shows the c8 fragment ion having a mass to charge ratio of 922, which is derived from the mutated beta chain (beta S), and which is also shown in FIG. 3B.

It can be seen by comparing FIGS. 3A-3C that the mutation in the beta chain in the AS and SS variants (FIGS. 3B and 3C) causes c8 fragment ions to be observed at a mass to charge ratio that is 30 Da lower than the c8 fragment ion from a non-mutated beta chain (FIG. 3A). A mass shift of 30 Da may be attributed to either a Threonine to Alanine mutation, or a Glutamic Acid to Valine mutation in the beta chain sequence. Within the beta chain sequence, three different possibilities exist for such a mutation, as shown in FIG. 4.

Figure 4:
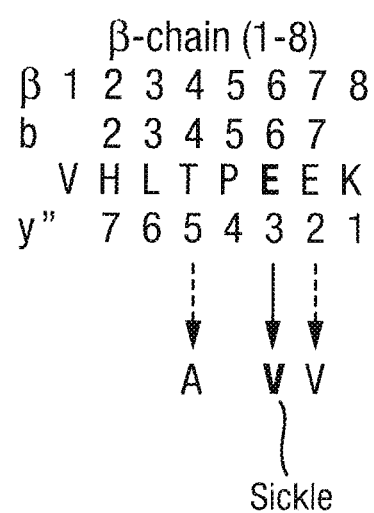
FIG. 4 shows the sequence for a haemoglobin beta chain and three possible mutations of the amino-acids.

FIG. 4 shows the amino-acid sequence for a non-mutated beta chain, together with the above-described three different possible mutations that would give rise to a 30 Da mass shift. At position 4 in the beta chain there is shown a potential mutation of Threonine to Alanine (T-A mutation), and at position 7 there is shown a potential mutation of Glutamic Acid to Valine (E-V mutation). These two mutations are "non-listed" and are not thought to be clinically significant. At position 6 in the beta chain there is shown a potential mutation of Glutamic Acid to Valine (E-V mutation). This mutation is known to cause sickle cell disease in homozygous cases, and may be asymptomatic in heterozygous cases. FIG. 4 also shows how the mutations would affect the b- and y-fragment ions.

The spectra in FIGS. 2B-2C and FIGS. 3B-3C show the putative location of the mutation, i.e. at the beta chain. However, it may be desirable to determine the precise location of the mutation in the AS and SS forms in order to determine if the mutation is clinically significant. This may be achieved by performing the second mode described above in relation to FIG. 1. In this mode, c8 fragment ions observed in the experiments of FIGS. 3A-3C may be selected and isolated. The isolated c8 fragment ion may then be subjected to Collisionally Induced Dissociation (CID) so as to produce sequence ions, as shown in the spectra of FIGS. 5A-5C. The sequence ions may then be used to determine the location of the mutation, and hence whether the mutation is clinically significant or not.

FIG. 5A shows the spectrum obtained by CID fragmentation of the c8 ion observed in FIG. 3A, i.e. for a normal (AA) blood sample. The b6 ion in this spectrum appears at its expected mass for a non-mutated sample. Referring back to FIG. 4, this indicates that the Glutamic Acid to Valine (E-V) mutation at position 6 in the beta chain has not occurred and that the patient providing this sample does not have sickle cell disease. The y2 and b4 ions in this spectrum also appear at their expected masses for a non-mutated sample. Again referring to FIG. 4, this indicates that the clinically insignificant Threonine to Alanine (T-A) mutation at position 4 in the beta chain has not occurred, and that the clinically insignificant Glutamic Acid to Valine (E-V) mutation at position 7 in the beta chain has not occurred.

FIG. 5B shows the spectrum obtained by isolating the c8 ions observed at a mass to charge ratio of around 922 in FIG. 3B, and then fragmenting these ions by CID, i.e. fragmenting the mutated c8 ions for the heterozygous (AS) blood sample. The b6 ion in this spectrum is located at a mass 30 Da below its expected mass for a non-mutated sample. Referring back to FIG. 4, this indicates that the Glutamic Acid to Valine (E-V) mutation at position 6 in the beta chain has occurred, indicating that the sample is either homozygous or heterozygous. It may be determined that the sample is a heterozygous sample by determining that both mutated an unmutated beta chains are present (e.g. from the MS spectrum shown in FIG. 2B). Alternatively, or additionally, it may be determined that the sample is a heterozygous sample by determining that c8 fragment ions having a mass to charge ratio of around 952 are generated in the first generation fragment ions (i.e. determining that the non-mutated c8 fragment ions shown in FIG. 3B are generated). Alternatively, or additionally, the sample may be determined to be heterozygous by fragmenting the first generation ions and detecting the presence of product ions generated from the fragmentation of unmutated c8 ions, i.e. from c8 ions at m/z 952. Data is not shown for this, but it would essentially correspond to that shown in FIG. 5A. Alternatively, or additionally, it may be determined that the sample is heterozygous, rather than homozygous, by determining that the mass shift in the b6 ions indicate a mutation and that the intensity of the b6 ion peak is below a threshold value.

The y2 and b4 ions in the spectrum of FIG. 5B appear at their expected masses for a non-mutated sample, indicating that the clinically insignificant Threonine to Alanine (T-A) mutation at position 4 in the beta chain and the clinically insignificant Glutamic Acid to Valine (E-V) mutation at position 7 in the beta chain have not occurred.

FIG. 5C shows the spectrum obtained by isolating the c8 ions observed at a mass to charge ratio of around 922 in FIG. 3C, and then fragmenting these ions by CID, i.e. fragmenting the mutated c8 ions for the homozygous (AS) blood sample. The b6 ion in this spectrum is located at a mass 30 Da below its expected mass for a non-mutated sample. Referring back to FIG. 4, this indicates that the Glutamic Acid to Valine (E-V) mutation at position 6 in the beta chain has occurred, indicating that the sample is either homozygous or heterozygous. It may be determined that the sample is a homozygous sample by determining that only the mutated beta chain, and not the unmutated beta chain, is present (e.g. from the MS spectrum shown in FIG. 2C). Alternatively, or additionally, it may be determined that the sample is a homozygous sample by determining that c8 fragment ions having a mass to charge ratio of around 952 are not generated in the first generation fragment ions (i.e. determining that the non-mutated c8 fragment ions shown in FIGS. 3A and 3B are not generated). Alternatively, or additionally, it may be determined that the sample is homozygous, rather than heterozygous, by determining that the mass shift in the b6 ions indicate a mutation and that the intensity of the b6 ion peak is above a threshold value. The y2 and b4 ions in this spectrum appear at their expected masses for a non-mutated sample, indicating that the "non-listed" Threonine to Alanine (T-A) mutation at position 4 in the beta chain and the "non-listed" Glutamic Acid to Valine (E-V) mutation at position 7 in the beta chain have not occurred.

Accordingly, once a 30 Da mass shift has been detected by the methods used to obtain the spectra in FIG. 2A-2C or 3A-3C, thus flagging a potential mutation listed as being of clinical interest, the technique of FIGS. 5A-5C may be used to identify the location of the mutation and whether the mutation is actually a mutation of clinical significance.

Although the present invention has been described with reference to various embodiments, it will be understood by those skilled in the art that various changes in form and detail may be made without departing from the scope of the invention as set forth in the accompanying claims.

For example, the approach described above may detect haemoglobin variants by detecting the location of a mass shift that is expected to occur if that variant is present. Alternatively, the above-described approach may be applied to detecting other clinically significant variants by detecting the location of a mass shift that is expected to occur if that variant is present. For example, the technique may be used to detect Hb Lepores or, for example, to detect any of the conditions listed below:

| Name | Mutation | Symptoms (homozygote or heterozygote) |
|---|---|---|
| Hb S | β6 (Glu to Val) | Sickle Cell Disease or asymptomatic |
| Hb C | β6 (Glu to Lys) | Mild anaemia or asymptomatic |
| Hb E | β26 (Glu to Lys) | Thalassemia minor or mild microcytosis |
| Hb D-Punjab | β121 (Glu to Gln) | Mild anaemia or asymptomatic |
| Hb O-Arab | β121 (Glu to Lys) | Mild anaemia or asymptomatic |

Although the embodiments described above relate to detecting variants of haemoglobin, the invention may be used to detect variants of other proteins in blood or other biological samples.

The invention claimed is:

1. A method of mass spectrometry comprising:
introducing a blood sample into a mass spectrometer system without subjecting said blood sample to liquid chromatography or digestion;
using Atmospheric Pressure Electron Capture Dissociation ("Ap-ECD") or Atmospheric Pressure Electron Transfer Dissociation ("Ap-ETD") to subject said blood sample to fragmentation so as to cause haemoglobin proteins to dissociate to form first protein fragment ions; and
fragmenting at least some of said first protein fragment ions to form second fragment ions, wherein the step of fragmenting at least some of said first protein fragment ions comprises isolating a c8 fragment ion derived from a haemoglobin beta chain and then fragmenting the isolated c8 fragment ion so as to form the second fragment ions, wherein the isolated c8 fragment ion is fragmented using Collision Induced Dissociation ("CID").

2. The method of claim 1, wherein the step of using Ap-ECD or Ap-ETD to subject said blood sample to fragmentation comprises using said Ap-ECD or Ap-ETD to subject said blood sample to in-source fragmentation so as to cause the haemoglobin proteins to fragment to form the first protein fragment ions.

3. The method of claim 2, further comprising using said first protein fragment ions and/or said second fragment ions to identify the location of haemoglobin sequence mutations.

4. The method of claim 1, comprising
mass analysing said first protein fragment ions to obtain first spectral data; and
determining whether or not ions in the first spectral data are at mass-to-charge ratios corresponding to the mass-to-charge ratios at which ions would be detected if the haemoglobin proteins are normal, unmutated haemoglobin; and
optionally, further comprising providing an indication that the haemoglobin proteins are normal unmutated haemoglobin if the ions in the first spectral data are at mass-to-charge ratios corresponding to the mass-to-charge ratios at which ions would be detected if the haemoglobin proteins are normal unmutated haemoglobin.

5. The method of claim 1, comprising
mass analysing said first protein fragment ions to obtain first spectral data; and
determining from the first spectral data if an ion is present at a mass-to-charge ratio corresponding to the mass-to-charge ratio at which an ion would be detected if the haemoglobin proteins are a mutated non-normal variant; and
optionally, further comprising providing an indication that the haemoglobin proteins are a mutated variant of haemoglobin.

6. The method of claim 1, further comprising using said first protein fragment ions and/or said second fragment ions to identify the location of haemoglobin sequence mutations.

7. The method of claim 6, comprising
mass analysing the second fragment ions to obtain second spectral data; and
determining from the second spectral data if an ion is present at a mass-to-charge ratio corresponding to the mass-to-charge ratio at which an ion would be detected if the haemoglobin proteins are a non-normal mutated variant.

8. The method of claim 7, comprising determining that an ion in the second spectral data has a mass-to-charge ratio that differs from the mass-to-charge ratio of an ion that would be observed if normal unmutated haemoglobin had been analysed, and that differs by an amount that corresponds to a mass difference caused by the haemoglobin proteins being a non-normal variant or caused by a mutation/substitution of an amino acid of normal haemoglobin for another amino acid.

9. The method of claim 8, wherein the mass difference is 30 Da; and/or wherein the mass difference corresponds to a mutation of glutamic acid to valine.

10. A method of mass spectrometry for determining if a mutated variant of a target protein is present in a sample, comprising:
introducing the sample comprising a target protein into a mass spectrometer, wherein the sample is not subjected to liquid chromatography or digestion prior to being introduced into the mass spectrometer;
subjecting the sample to fragmentation so as to cause said target protein to dissociate to form first protein fragment ions, wherein said fragmentation is Atmospheric Pressure Electron Capture Dissociation ("Ap-ECD") or Atmospheric Pressure Electron Transfer Dissociation ("Ap-ETD"), and wherein said first protein fragment ions comprise c-type fragment ions formed by said Ap-ECD or Ap-ETD;
fragmenting at least some of said first protein fragment ions to form second fragment ions, wherein the step of fragmenting at least some of said first protein fragment ions comprises:
isolating one of said c-type fragment ions from other fragment ions and then fragmenting the isolated c-type fragment ion so as to form the second fragment ions, wherein the isolated c-type fragment ion is fragmented using Collision Induced Dissociation ("CID"), and wherein the isolated c-type fragment ion is a c8 fragment ion derived from a haemoglobin beta chain;

the method further comprising: mass analysing said second fragment ions to obtain first spectral data; and determining if an ion in the first spectral data has a first mass-to-charge ratio that differs from a second mass-to-charge ratio by an amount that corresponds to a mass difference that would be caused by the target protein being a mutated variant of said target protein, wherein the second mass-to-charge ratio is the mass-to-charge ratio of an ion that would be observed if said target protein is a normal unmutated version of said target protein.

11. The method of claim 10, wherein:
said sample is, or comprises: blood; whole-blood; diluted blood; or diluted whole blood; and/or
wherein the target protein is subjected to ionisation prior to said step of subjecting the sample to fragmentation such that target protein ions are fragmented to form the first protein fragment ions and optionally wherein the target protein is ionised in an ion source to form the target protein ions.

12. The method of claim 10, further comprising, when it is determined that an ion in the first spectral data has said first mass-to-charge ratio:
using the first mass-to-charge ratio of said ion in the first spectral data to identify a location of a mutation within a protein sequence of the target protein and identifying a type of variant of the target protein in the sample from the identified location; or
using the value of said mass difference to identify a type of mutation in a sequence of the target protein and identifying a type of variant of the target protein in the sample from the identified type of mutation.

13. The method of claim 10, wherein the target protein is mass analysed in a precursor ion mode without first being fragmented; wherein when it is determined that an ion in the first mass spectral data has said first mass-to-charge ratio:
a related precursor ion detected in said precursor ion mode is considered and/or indicated as being a mutated precursor ion from a mutated variant of the target protein; and the method further comprises:
determining whether or not precursor ions detected in said precursor ion mode contain a precursor ion corresponding to a non-mutated version of the related precursor ion; and
when it is determined that the precursor ions contain both said mutated precursor ion and said non-mutated version of the related precursor ion, determining that a mutated variant of the target protein is a heterozygous variant of the target protein; and
when it is determined that the precursor ions contain said mutated precursor ion and not said non-mutated version of the related precursor ion, determining that a mutated variant of the target protein is a homozygous variant of the target protein.

14. The method of claim 10, wherein when it is determined that an ion in the first mass spectral data has said first mass-to-charge ratio:
a related first fragment ion that is fragmented to form the second fragment ions is considered and/or indicated as being a mutated first fragment ion from a mutated variant of the target protein; and the method further comprises:
determining whether or not the first protein fragment ions contain a fragment ion corresponding to a non-mutated version of the related first fragment ion; and
when it is determined that the first protein fragment ions contain both said mutated first fragment ion and said non-mutated version of the related first fragment ion, determining that a mutated variant of the target protein is a heterozygous variant of the target protein; and
when it is determined that the first protein fragment ions contain said mutated first fragment ion and not said non-mutated version of the related first fragment ion, determining that a mutated variant of the target protein is a homozygous variant of the target protein.

15. A method of identifying a type of haemoglobin variant in a blood sample comprising a method as claimed in claim 10.

* * * * *